United States Patent
Strohhöfer

(10) Patent No.: US 10,086,127 B2
(45) Date of Patent: Oct. 2, 2018

(54) DETECTING DEVICE FOR A MEDIUM INSIDE A TUBE PORTION

(71) Applicant: B. BRAUN AVITUM AG, Melsungen (DE)

(72) Inventor: Christof Strohhöfer, Vienna (AT)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 15/681,017

(22) Filed: Aug. 18, 2017

(65) Prior Publication Data

US 2018/0055987 A1 Mar. 1, 2018

(30) Foreign Application Priority Data

Aug. 30, 2016 (DE) .................... 10 2016 116 100

(51) Int. Cl.
*A61M 1/36* (2006.01)
*G01N 21/94* (2006.01)
(Continued)

(52) U.S. Cl.
CPC .......... *A61M 1/3626* (2013.01); *A61M 1/367* (2013.01); *G01N 21/0303* (2013.01);
(Continued)

(58) Field of Classification Search
CPC ....... G01N 35/1016; G01N 2035/1025; G01N 21/94; G01N 21/8806; G01N 21/6456;
(Continued)

(56) References Cited

U.S. PATENT DOCUMENTS 6,362,887 B1   3/2002  Meisberger
6,574,490 B2 * 6/2003  Abbink ................ A61B 5/0075
                                                356/39

(Continued)

FOREIGN PATENT DOCUMENTS

DE          19825518 A1    12/1999
DE       102009014080 A1    9/2010
(Continued)

OTHER PUBLICATIONS

German Search Report for German Application No. 10 2016 116 100.4, dated Apr. 28, 2017 with translation, 13 Pages.
Extended European Search Report for European Application No. 17 186 367.3, dated Feb. 15, 2018, including English translation, 28 pages.

*Primary Examiner* — Sang Nguyen
(74) *Attorney, Agent, or Firm* — RatnerPrestia

(57) ABSTRACT

A detecting device for a medium inside a tube portion comprises at least one light source being arranged at a first position relative to the tube portion adapted to be transilluminated with light and being configured to irradiate light onto the tube portion, a detector unit being arranged at a second position relative to the tube portion and being configured to receive light from the at least one light source passed through the tube portion and to analyze a medium inside the tube portion in a spatially resolving manner, and a homogenizing device being arranged at a position between the at least one light source and the tube portion and being configured, for detecting and quantifying differences in brightness due to local differences of the medium inside the tube portion, to create a homogenous and/or isotropic distribution of the light from the at least one light source before the light enters into the tube portion.

13 Claims, 3 Drawing Sheets

(51) Int. Cl.
*G01N 21/88* (2006.01)
*G01N 21/64* (2006.01)
*G01N 21/03* (2006.01)
*G01N 21/25* (2006.01)
*G01N 21/53* (2006.01)
*G01N 21/85* (2006.01)
*G01N 21/17* (2006.01)

(52) U.S. Cl.
CPC .......... *G01N 21/255* (2013.01); *G01N 21/53* (2013.01); *G01N 21/6456* (2013.01); *G01N 21/85* (2013.01); *G01N 21/8806* (2013.01); *G01N 21/94* (2013.01); *A61M 2205/3313* (2013.01); *G01N 2021/0392* (2013.01); *G01N 2021/178* (2013.01); *G01N 2021/1765* (2013.01); *G01N 2021/1772* (2013.01); *G01N 2021/6463* (2013.01); *G01N 2201/062* (2013.01); *G01N 2201/0631* (2013.01)

(58) Field of Classification Search
CPC ......... B01L 9/06; G02B 21/002; G02B 21/06; G02B 21/248; G02B 21/365; A61M 1/3626; A61M 2205/3313
See application file for complete search history.

(56) References Cited

U.S. PATENT DOCUMENTS

| | | | |
|---|---|---|---|
| 8,675,195 B2 | 3/2014 | Ihlefeld et al. | |
| 2003/0007147 A1* | 1/2003 | Johnson | G01J 3/02 356/326 |
| 2004/0080745 A1 | 4/2004 | Kvassheim | |
| 2004/0141179 A1 | 7/2004 | Fry et al. | |
| 2007/0035820 A1* | 2/2007 | Grimes | B01L 9/06 359/368 |
| 2007/0052953 A1* | 3/2007 | Hill | G01N 21/4738 356/237.2 |
| 2011/0115905 A1 | 5/2011 | Beumer et al. | |
| 2011/0249255 A1* | 10/2011 | Bentien | G01N 15/1434 356/51 |
| 2012/0032618 A1 | 2/2012 | Stöger | |
| 2015/0276589 A1* | 10/2015 | Wagner | G01N 21/39 356/440 |

FOREIGN PATENT DOCUMENTS

| | | |
|---|---|---|
| EP | 0467804 A1 | 1/1992 |
| EP | 2264512 A1 | 12/2010 |
| WO | 0039573 A1 | 7/2000 |

* cited by examiner

DETECTING DEVICE FOR A MEDIUM INSIDE A TUBE PORTION

CROSS REFERENCE TO RELATED APPLICATIONS

This application claims priority to German application DE 10 2016 116 100.4 filed Aug. 30, 2016, the contents of such application being incorporated by reference herein.

FIELD OF THE INVENTION

The invention relates to a detecting device for a medium inside a tube portion and especially relates to a detecting device of the kind that incorporates a lighting system for imaging sensors on medical apparatuses, for example those in which blood tubing systems are applied.

BACKGROUND OF THE INVENTION

In dialysis, the blood of the patient flows through a tubing system of an extracorporeal blood circulation. On the one hand, the extracorporeal guiding of blood enables easy access to the patient's blood so as to determine analytical parameters from the same. On the other hand, the extracorporeal guiding of blood constitutes a risk factor in dialysis treatment, as in this way undesired foreign matter such as impurities or air may be supplied to the patient.

The fields of application of most various sensor systems focusing on the detection of such foreign matter are correspondingly manifold. Accordingly, special attention is paid to sensor methods which are capable of analyzing the blood and, respectively, the content of the blood tubing system in a contactless and non-destructive manner. Contactless in this context means that the blood does not contact any material other than the standard material of the tubing system. Thus, on the one hand, the occurrence of additional centers of coagulation or inflammation is avoided. On the other hand, manufacturing costs are minimized as it is not necessary to combine different materials and structures. Non-destructive in this context means that the measuring technique does not affect, weaken or even destroys the cellular or molecular components of the blood. This is especially important as the formation of red blood cells is impaired in dialysis patients and each loss of the same may permanently impair the health condition and the well-being of the patient.

It is known that optical technologies are suited for contactless and non-destructive analysis of substances. Light may interact with the analyte without any direct contact between the analyte and the light source or detector and only under extreme conditions will result in a damage of cells, for example. Such extreme conditions may be easily avoided by a smart design of the sensor.

The use of optical sensors in dialysis is known. These include e.g. hematocrit sensors (on the basis of red and infrared light), red detectors (indicating the presence of blood in the blood tubing system) and blood leakage detectors (measuring reddening in dialysis solution in the dialysis solution circuit) or analytical sensors in the dialysis solution circuit for real-time monitoring, for example those permitting determination of a dialysis dose during therapy. Said sensors measure at least quasi balanced states, i.e. they indicate a concentration, a coloring or the presence of a substance in the blood, for example. For this, the entirety of the light incident on the detector is analyzed and processed to form a measuring value. For this reason, no special demands are made to the lighting system of said sensors. In general, said sensors are neither adapted to make any statements about short-term disturbances and, respectively, are even negatively influenced by the same, nor are they capable of determining a measuring value in a space-resolved manner, i.e. at various locations inside the tube.

In several applications such as the detection of air bubbles or dissolved impurities, for example, spatial resolution is favorable in order to identify and quantify said air bubbles or impurities (air bubbles e.g. as to volume, impurities as to size and structure). For space-resolved measurement detector arrays which are capable of reproducing spatial information by the combination of a plurality of pixels are required. A simple example of such measuring system based on spatial resolution are cameras imaging the system to be examined onto a CMOS or CCD element and thus providing the spatial information for analysis. Other than in the case of optical sensors, in such imaging measuring systems a homogenous illumination of the entire detector array is an important characteristic. If the illumination of one pixel of the detector array is weaker than that of another one, this is traced back to local interaction between the light and the analyte. If, instead of this, a different illumination is caused by inhomogeneous distribution of the incident light, this results in misinterpretation of the measurement.

For measurement on a tube, further criteria have to be observed. A tube as a substantially cylindrical object may act, on the one hand, as a lens resulting in different illumination of the detector array, as is schematically shown in FIG. 1. The lens effect shown in FIG. 1 results in inhomogeneous light distribution on a detector unit when a tube is transilluminated. The effect is moreover dependent on whether a fluid and which type of fluid is provided therein.

On the other hand, in the case of transillumination of the tube section, the optical paths of the light through the medium inside the tube are different (see FIG. 2). This, too, usually results in inhomogeneous illumination of the detector array, as in the case of homogeneous transillumination of a tube the light beams at the rim of the tube interact less strongly than light beams in the middle of the tube with the medium inside the tube. This equally results in an inhomogeneous light distribution on the detector unit, as light penetrating at the rim of the tube is absorbed less than light penetrating the central area of the tube. Differences in illumination analogous hereto may occur when the illumination system consists of a point light source or few point light sources such as arrays of light-emitting diodes or LED.

As afore-described, in prior art merely homogeneous illumination of a flat surface has been described.

SUMMARY OF THE INVENTION

Therefore, an object underlying the invention is to provide a detecting device for a medium inside a tube portion which permits, based on homogeneous illumination of the interior of the tube portion, proper imaging of the tube interior with imaging and/or space-resolved optical methods.

In accordance with the invention, this object is achieved by a detecting device for a medium inside a tube portion comprising the features of the independent claim. Advantageous developments are the subject matter of the enclosed subclaims.

The general idea underlying the invention is to provide homogeneously distributed light for an imaging optical sensor. The sensor constitutes at least part of a detector unit analyzing a medium inside a tube or at least a tube portion. The provided light is appropriately homogenized so that differences in brightness which are due to local differences of the medium inside the tube or tube portion can be identified and quantified (evaluated). The local differences may be, for example, variations in density of an absorbing substance, inclusions of different mediums (e.g. air in a liquid), solid particles in a liquid or the like. The tube or tube portion may be arranged either between a light source and a detector unit (detector array) or the light source and the detector unit may be arranged on the same tube side and/or at a predetermined angle relative to each other.

A homogenizing device for the light is arranged between the light source and the tube so that the tube is indirectly illuminated by the light source. For example, a scattering plate, a diffuser film or in general a transparent roughened medium may be used as a homogenizing device. The afore-described basic principle in which basically a homogenizing device for the light is placed between the light source and the tube instead of direct illumination of the tube by a light source is schematically shown in FIG. 3.

Especially advantageous embodiments of the homogenizing device at least partially comprise convex and/or concave surfaces and/or a variable absorbing function, i.e. combinations of scattering and/or diffuser members with an absorbing material, by stepwise or gradually occurring introduction of absorbing substances into predetermined areas of the homogenizing device perpendicularly to the direction of light propagation. A preferred variable absorbing function incorporates stronger light absorption in predetermined outer areas or marginal areas of the homogenizing device, the light absorption being attenuated toward a central area of the homogenizing device.

In detail, an object is achieved by a detecting device for a medium in a tube portion comprising: at least one light source being arranged at a first position relative to a tube portion adapted to be transilluminated by light and being configured to irradiate light onto the tube portion; a detector unit being arranged at a second position relative to the tube portion and being configured to receive light from the at least one light source passed through the tube portion and to analyze a medium in the tube portion in a spatially resolving manner; and a homogenizing device being arranged at a position between the at least one light source and the tube portion and being configured to produce a homogeneous and/or isotropic distribution of the light from the at least one light source before the light enters into the tube portion, for detecting and quantifying differences in brightness due to local differences of the medium inside the tube portion.

Preferably, in a geometrical arrangement for transmission measurement the at least one light source is arranged on a first side of the tube portion and the detector unit is arranged on a second side of the tube portion so that the tube portion is located between the at least one light source and the detector unit.

As a preferred alternative, in a geometrical arrangement for reflection measurement the at least one light source and the detector unit are arranged with respect to the tube portion on the same side and, accordingly, adopt a predetermined angle relative to each other.

Preferably, the homogenizing device is a scattering plate, a diffusor film or a transparent medium having a roughened surface.

The homogenizing device is preferably arranged to be located as closely as possible to the tube portion.

Preferably, at least a first wall and a second wall are provided between which the at least one light source and/or the homogenizing device is/are arranged. Relating to configuration, the first and/or second wall(s) may be reflective so as to reduce possible light losses along the light path, or may be non-reflective and/or have a predetermined coloring, for example black, so as to avoid undesired reflections by e.g. a smooth surface of a tube made from e.g. plastic material.

Preferably, an imaging optical system is arranged ahead of the detector unit and/or between the at least one light source and the homogenizing device.

Preferably, the size of the homogenizing device is in conformity with at least the size of a field of view of the detector unit. With a given flow rate of the medium inside the tube portion and a given receiving rate of the detector device a field of view of the detector unit and a minimum dimension of the homogenizing device in the longitudinal direction of the tube portion can be determined to be GF=FR/AR, and a minimum dimension of the homogenizing device in the transverse direction of the tube portion may be at least equal to the total diameter of the tube portion.

Preferably, the at least one light source is configured to completely illuminate an expansion of the homogenizing device in the longitudinal direction of the tube portion, wherein for complete illumination an appropriately adapted shape of the at least one light source or a plurality of light source elements and/or beam-forming elements is provided in a light path.

Preferably, in the homogenizing device along a direction perpendicularly to the transilluminating direction and light propagating direction, respectively, in predetermined areas of the homogenizing device predetermined concentrations of a light-absorbing substance are introduced which provide a variably light-absorbing function of the homogenizing device. Advantageously, such concentrations may be introduced stepwise or gradually variably and insofar may provide a variable absorbing function for light of the homogenizing device by which unequal optical path lengths in the medium inside the tube or tube portion and an unequal lighting or illumination of a detector array resulting therefrom can be compensated or at least significantly reduced.

Preferably, a medical apparatus may advantageously comprise a detecting device as described in the foregoing. Further advantageously, a medical apparatus may be in the form of a machine for extracorporeal blood treatment, for example a dialysis machine.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
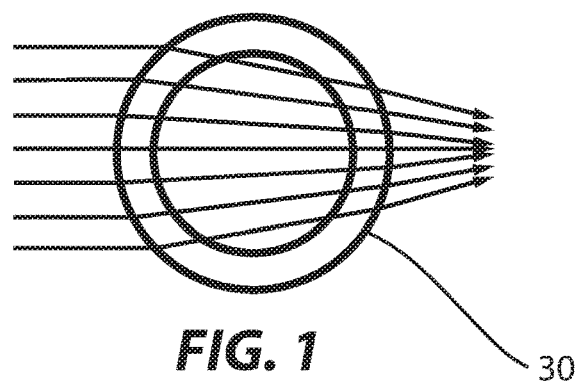
FIG. 1 schematically shows a lens effect which, when a tube is transilluminated, results in an inhomogeneous light distribution on a detector unit.

It is noted that in the drawing like or equally acting elements and components are denoted with like reference numerals and are not redundantly described.

Figure 3:
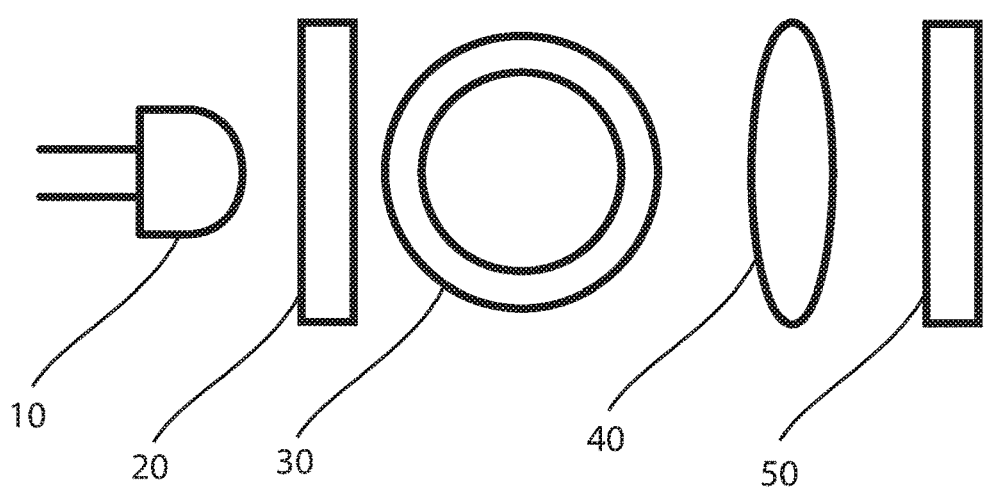
FIG. 3 simplifies and schematically shows a structure of a detecting device for locally resolved analysis of a medium inside a tube or tube portion according to the first embodiment which is geometrically configured for transmission measurement.

FIG. 3 schematically shows and simplifies a structure of a detecting device in the form of an optical sensor for locally resolved analysis of a medium inside a tube or tube portion according to a first embodiment.

In the first embodiment, a transmission geometry is used in which a light source 10, for example a light-emitting diode or LED, transilluminates a tube or tube portion 30 guiding a medium and light from the light source 10 impinges on a detector array 50 after passing through the tube or tube portion 30. The detector array 50 in this embodiment is understood to be a detection, sensor or detector unit which includes at least one detecting or sensor element. Especially, in this embodiment the detector array 50 may be an image-recording unit and/or image processing unit and may at least be adapted to generate detecting signals which can be pictorially evaluated. Upstream of the detector array 50 an imaging optical system 40, for example a lens arrangement, a camera lens and the like may optionally be arranged.

The light source 10 may be selected, depending on a respective application, from e.g. lamps such as deuterium lamps or Hg lamps for measuring problems in the UV range, halogen lamps for measuring problems in the range of visible and infrared light and/or light-emitting diodes or LED which may either have a broad emission spectrum and consequently emit almost white light or emit light only within a narrow band around a particular wavelength. Especially LED are applicable with light emission both in the UV range and in the visible and infrared spectral range. Furthermore, lasers which are adapted to emit very narrow-band light from the UV range via the range of visible light to the infrared range may be applied.

In order to reach a sufficient degree of homogeneous illumination further a homogenizing device 20 for the light from the light source 10 is arranged between the light source 10 and the tube portion 30.

The homogenizing device 20 is arranged so that the light of a spotlight used in this embodiment for example as a light source 10 loses its preferred direction in space before passing through the tube or tube portion 30 and is isotropically irradiated onto the tube or tube portion 30. The use of the homogenizing device 20 is useful especially in spectral ranges in which wavelengths are small as compared to the geometric dimensions of the field of view.

Further optionally a lens arrangement (not shown) between the light source 10 and the homogenizing device 20 can vary the light irradiation of the light source 10 in a predetermined way before its light is incident on the homogenizing device 20.

Preferred dimensions and a total size of the homogenizing device 20 can be derived from the marginal conditions of each application. A salient factor in this respect is the image field of involved components, wherein basically the dimensions of the homogenizing device 20 should at least be in conformity with the dimensions of the field of view of the detector array 50. In the case of an in-flow measurement, i.e. measurement with a flowing medium, moreover also a velocity of the image recording by the detector array 50 has to be included.

For example, in a system incorporating the configuration of this embodiment blood can be pumped through the tube or tube portion 30 at a rate FR and in this case the detecting device as detection system is intended to identify and measure air bubbles in the blood. The detection system has a recording rate AR, for example, i.e. a predetermined number, e.g. N, of records per time unit, e.g. per second, can be generated.

In the afore-mentioned exemplary case, this means that in intervals of 1/N seconds one record at a time can be made. In order to ensure that no air bubble remains undiscovered, the system has to be designed so that with a given flow rate of the blood an air bubble is retained in the field of view of the detecting sensor for at least 1/N seconds. Therefrom, it is resulting for the field of view of the detecting sensor GF (along the tube) according to the following equation (1):

$$GF=FR/AR \tag{1}$$

At the same time, this is the minimum dimension of the homogenizing device 20 in the longitudinal direction of the tube or tube portion 30. Moreover, in the transverse direction of the tube or tube portion 30 the dimension of the homogenizing unit 20 has to be equal to or larger than the total diameter of the tube or tube portion 30. Due to the effects described in the beginning with reference to FIG. 1 and FIG. 2, a dimension of the homogenizing device 20 merely corresponding to the inner diameter of the tube or tube portion 30 is not sufficient.

The dimensions of the homogenizing device 20 and, respectively, the size of the field of view moreover predetermine the embodiment of the light source 10.

Ideally, the entire homogenizing device 20 is irradiated with light. Especially in in-flow measuring systems the dimensioning along the tube or tube portion 30 may be definitely larger than the dimensioning transversely to the tube or tube portion 30.

Thus, the light source 10 has to be adapted for completely irradiating or illuminating an oblong homogenizing device 20, i.e. a homogenizing device 20 which is longer than wide. In order to achieve this, in this embodiment specific shapes of the light source 10 which further may be combined with beam-forming elements, or a number of plural smaller or spot-shaped light sources (spotlights) may be provided. In the case of smaller or spot-shaped light sources, they are preferably arranged so that the radiation fields thereof are sufficiently overlapping in the plane of the homogenizing device 20 so as to ensure complete illumination.

Figure 4:
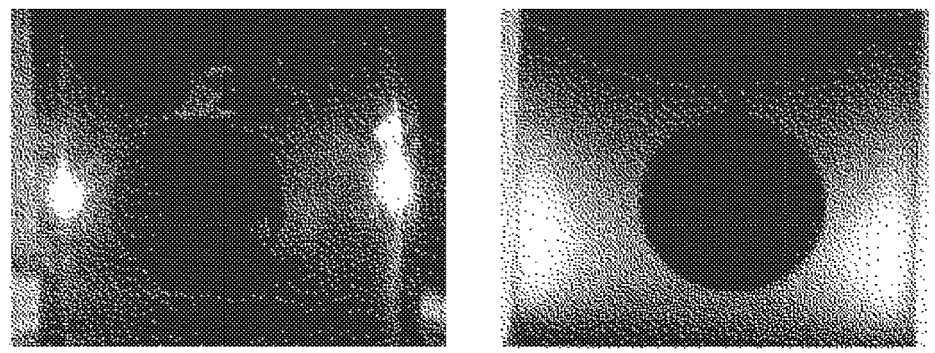
FIG. 4 illustrates an enhancement of illumination obtained by a homogenizing device.

FIG. 4 illustratively and schematically shows an enhanced illumination which may be obtained by the homogenizing device 20.

In a test rig, the tube or tube portion 30 was represented by a water-filled glass bulb having a diameter of 5 cm and an object to be imaged in a medium (water in this case) was represented by a plastic ball having a diameter of 1 cm.

The partial image on the left in FIG. 4 illustrates a bitmap representation of a picture without homogenizing device 20 and the partial image on the right in FIG. 4 shows a bitmap representation of a picture including the homogenizing device 20, experimentally in the form of a diffuser film, between the light source 10 and the glass bulb (tube or tube portion 30).

As is directly evident from FIG. 4, the quality of illumination when using the homogenizing device 20 is definitely increased. For, while in the left-hand partial image (without homogenizing device 20) the light can be identified as being localized primarily at the rim of the glass cylinder and the illumination of the liquid and the plastic ball is not sufficient to properly identify the contours of the plastic ball, the right-hand partial image (including the homogenizing device 20) shows a broad properly illuminated strip against the background of which the contour of the plastic ball is defined in a sufficiently proper manner so as to be able to measure the geometry of the ball. Still exiting differences in brightness between the rim and the center of the glass bulb are definitely reduced with respect to the left-hand partial image.

The best or most homogeneous illumination can be achieved when the homogenizing device 20 is disposed most closely to, i.e. as closely as possible upstream of, the tube or tube portion 30. The reason for this resides in the fact that homogenizing devices for light in the form of scattering disks or diffusor films, for example, scatter the light and, in this way, generate an as homogenous but also isotropic distribution of light as possible downstream of the homogenizing device 20. As a consequence, the lighting intensity decreases with an increasing distance from the homogenizing device 20 as the illuminated surface increases by reason of the radiation isotropy. At the same time, however, also the homogeneity of irradiation decreases mainly in marginal areas with the increasing distance from the homogenizing device 20. It is noted that in practice an achievable minimum distance from the homogenizing device 20 and the tube or tube portion 30 is basically determined also by an optical system used in a camera and the aperture angle and focusing range thereof.

Figure 5:
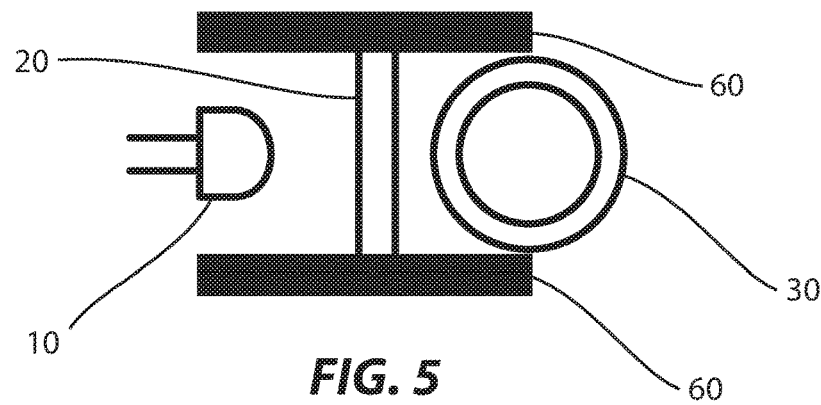
FIG. 5 simplifies and schematically shows a structure of a detecting device for locally resolved analysis of a medium inside a tube or tube portion according to a second embodiment in which a light conducting device is arranged to counteract a reduction of the lighting intensity downstream of the homogenizing device.

FIG. 5 illustrates a second embodiment comprising a light conducting device 60 being arranged to counteract a reduction of the illuminating intensity downstream of the homogenizing device 20. In this second embodiment, the light conducting device 60 is configured in at least the area between the homogenizing device 20 and the tube or tube portion 30 in the form of a light-reflective wall which surrounds at least the afore-mentioned area by covering the same and which reflects the light irradiated by the light source 10 by its inside. In this way, also light exiting the homogenizing device 26 under a large angle is incident on the tube or tube portion 30 after being reflected by the wall. The luminous efficiency can be further increased by the fact that the reflecting walls of the light conducting device 60 extend beyond the light source 10. In this case, even light already irradiated by the light source 10 under a large angle is initially incident on the homogenizing device 20 and then on the tube or tube portion 30. In total advantageously, light conducting devices such as, for example, light-reflective walls permit any positioning of the homogenizing device 20, as also the light scattered under an angle by the homogenizing device 20 is not lost but is incident on the tube.

It is noted that with reference to configuration and/or depending on an application, the light conducting device 60 may also or alternatively form a wall which is non-reflective and/or is kept in a predetermined coloring, for example black, by which undesired reflections by a smooth surface of a tube made e.g. from plastic material can be avoided or at least reduced.

Figure 6:
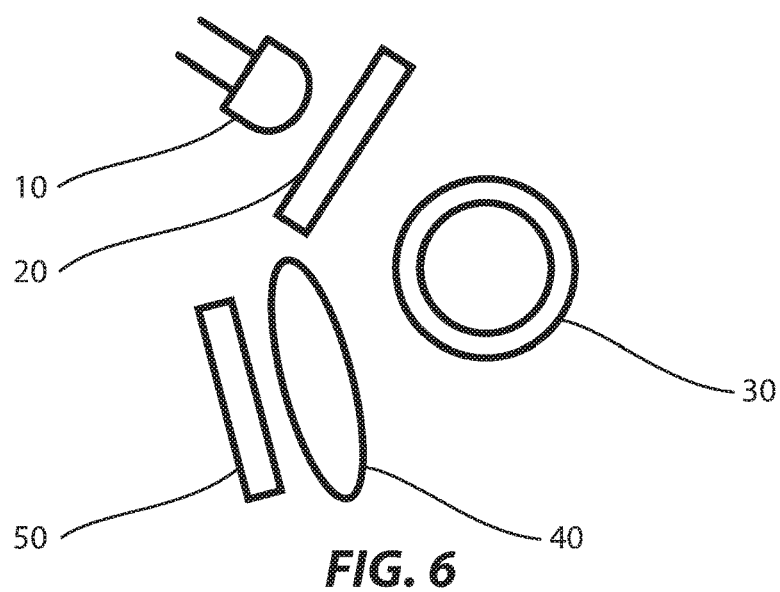
FIG. 6 simplifies and schematically shows a structure of a detecting device for locally resolved analysis of a medium inside a tube or tube portion according to a third embodiment which is geometrically configured for reflection measurement.

FIG. 6 simplifies and schematically shows a structure of a detecting device for locally resolved analysis of a medium inside a tube or tube portion according to a third embodiment which is geometrically configured for reflection measurement.

As an alternative to a transmission configuration as afore-described in connection with the first embodiment, it is possible to provide a geometric arrangement for reflection measurements. In this case, light reflected by the medium inside the tube or tube portion 30 is detected. Accordingly, the reflected light can be measured at any angle with respect to the incident light. Small angles are advantageous, as the light reflected there usually shows maximum intensity. In the reflection configuration care has to be taken that the homogenizing device 20 preferably does not restrict the field of view of the detector array, as otherwise light reflected by the tube or tube portion 30 first has to pass through the homogenizing device 20 again before it reaches the detector array 50 and, as a consequence, a loss of information may occur.

Depending on the angle between the incident light and the direction of detection, a plurality of further measuring problems can be solved by the configuration shown in FIG. 6 apart from measuring reflected light. For example, light scattered by the medium inside the tube or tube portion 30 can be measured. Said light is the more intense, the more inhomogeneous the medium, and consequently allows to conclude therefrom pollution or air inclusions present. An optimum angle between the light irradiating direction and the light detecting direction depends on the size of the elements to be measured.

Furthermore, by a configuration of the afore-mentioned type also imaging fluorescence measurements and/or luminescence measurements can be carried out on the medium inside the tube or tube portion 30. The fluorescence or luminescence is excited by the irradiated light. A wavelength-selective filter integrated in the detection path (not shown) is arranged for allowing the fluorescent light or the luminescent light to pass, but for withholding the exciting light. The detector array in this case then only detects the fluorescent light or the luminescent light. In the case of measurement of this type, preferably the angle between the irradiation direction and detection direction is preset in which the intensity of the exciting light incident on the detector is minimal.

As afore-described, the geometry of the tube or tube portion 30 constitutes additional challenges to the homogenous illumination of the field of view and the illumination in general may be improved by the use of the homogenizing device 20 and further by a specific configuration or design of the homogenizing device 20.

In particular the lens effect of the tube or tube portion 30 (see FIG. 1) may be compensated by a geometric design of the homogenizing device 20 in accordance with a scattering lens.

Figure 7:
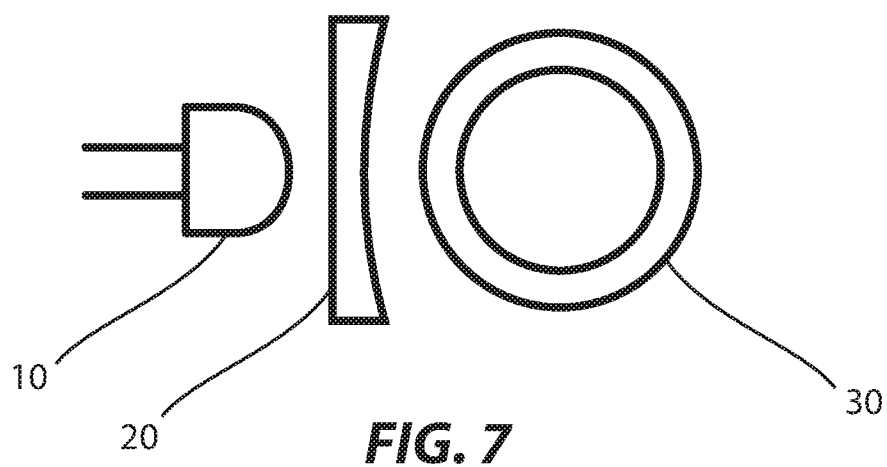
FIG. 7 shows a configuration of the homogenizing device applicable in a modification of the first to third embodiments in plano-concave shape.

In a modification of the afore-described embodiments as shown in FIG. 7, therefore the homogenizing device 20 may be plano-concave, i.e. having a planar surface on a side facing the light source 10 and a concave surface on an opposite side facing the tube or tube portion 30. Comparable effects can be achieved by other shapes including at least one concave surface, for example concave-concave or concave-planar embodiments of the homogenizing device 20. With designs saving construction space moreover also the homogenizing device 20 can be placed as closely as possible to the tube or tube portion 30.

Figure 8:
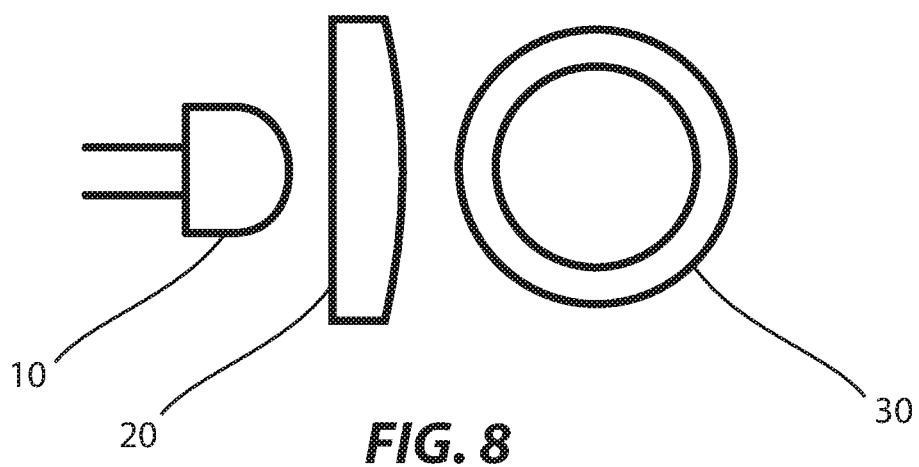
FIG. 8 shows a configuration of the homogenizing device applicable in an alternative modification of the first to third embodiments in plano-convex shape.

In another modification of the afore-described embodiments as shown in FIG. 8, furthermore the homogenizing device 20 may be configured to be plano-convex, i.e. having a planar surface on a side facing the light source 10 and having a convex surface on an opposite side facing the tube or tube portion 30. In the case of a plano-convex shape, the homogenizing device 20 is designed in the manner of a focusing lens and thus the homogenized light can be specifically intensified in a particular area of the tube or tube portion 30. Comparable effects can be achieved with convex-convex or convex-planar shapes.

Figure 9:
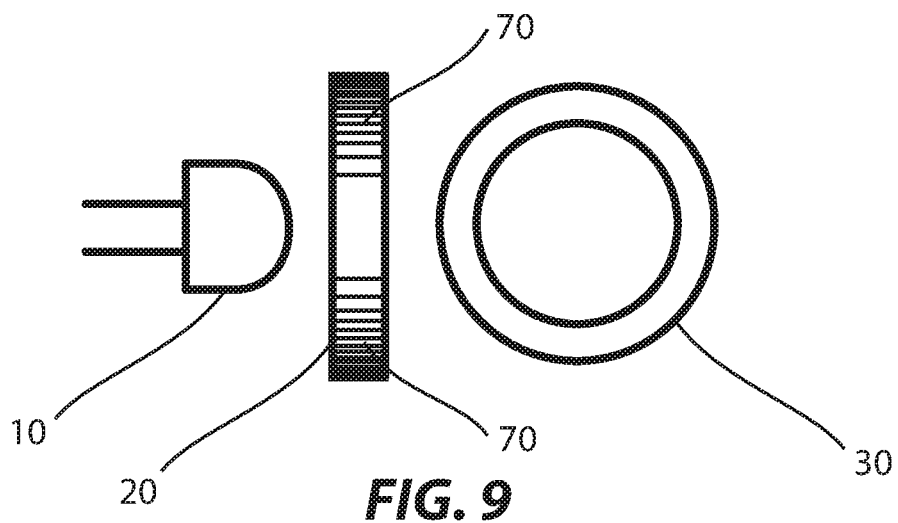
FIG. 9 shows a configuration of the homogenizing device applicable in another alternative modification of the first to third embodiments with increased absorption in an outer area and lower absorption in a central area.

In yet another modification of the afore-described embodiments as shown in FIG. 9, in addition the homogenizing device 20 can be configured to be differently absorbing in its course, for example with increased absorption in an outer area or marginal area and lower absorption in a central area. In FIG. 9 this is to be indicated, for example, at upper and lower edge areas when viewed as a side view and, respectively, at right and left edge areas when viewed as a top view.

Figure 2:
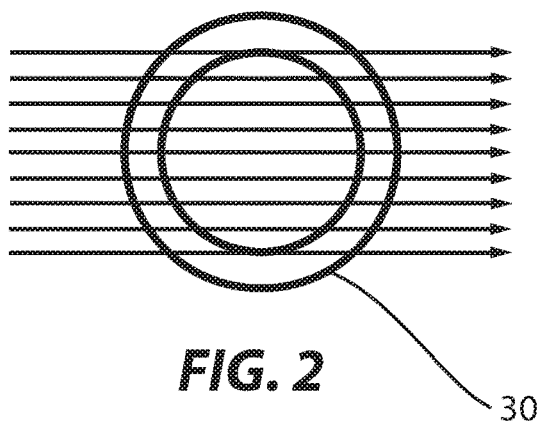
FIG. 2 schematically shows interaction of beams at the rim and in a central area of a tube with homogeneous transillumination of the tube, wherein marginal beams interact with a medium inside the tube less strongly than central beams and, due to different light absorption at the rim and in the central area, inhomogeneous light distribution is resulting on the detector unit.

With reference to FIG. 2, the problem shown in FIG. 2 of unequal optical path lengths in the medium inside the tube or tube portion 30 results in non-uniform illumination or lighting of the detector array 50 exactly when the medium inside the tube or tube portion 30 is absorbing light.

Such undesired absorption can be compensated or at least reduced with the homogenizing device 20. For this purpose, the homogenizing device 20 cannot be in the form of a pure and thus uniformly scattering disk, but substances absorbing light incident at predetermined positions or areas of the homogenizing device 20 may be provided to be attached as absorber 70. In this way, the incident light can be specifically absorbed at the predetermined positions or areas (i.e. more or less strongly with respect to a reference region of the homogenizing device 20).

When said absorbers 70 are introduced in the area of the upper edge and/or the lower edge of the homogenizing device 20, for example, as schematically indicated in FIG. 9, incident light is absorbed on the upper side and/or the lower side of the tube or tube portion 30 and thus is attenuated there. It is possible in this way to further homogenize the light incident on the detector array 50 and overdrive and crosstalk of detectors of the detector array 50 can be reduced, as is evident in the left-hand partial image of FIG. 4, for example.

In detail, FIG. 9 illustrates a configuration of the homogenizing device 20 in which absorbing substances are integrated in the homogenizing device 20 in such way that a gradual concentration profile of said substances is resulting. In FIG. 9, this concentration profile is indicated by the different cross-line density along the height direction of the homogenizing device 20. Accordingly, in each of upper and lower areas of the homogenizing device 20 the concentration of the added substances is higher and in a central area it is lower, on the other hand. When the light absorbing profile formed in this way is appropriately adapted to the geometric conditions of the tube or tube portion 30 and to the optical characteristics of the medium, crosstalk of the detectors of the detector array 50 at the edges of the detector array 50 can be avoided. Absorption can be introduced to the homogenizing device 20 by specific modification of the base material and/or by combining different materials, for example by providing an absorbing film having a predetermined absorbing profile which is applied or glued to the homogenizing device.

A comparable effect can be achieved using a stepped profile of absorption in the homogenizing device 20. Accordingly, by appropriately modifying the material at a suitable position and/or by adding absorbing material in the marginal areas absorption may be created in the upper and lower marginal areas of the homogenizing device 20 only.

As described in the foregoing, according to aspects of the invention inhomogeneities inside a tube or tube portion through which liquid medium flows can be resolved with detection of the inhomogeneities resolved in space and time.

Especially when returning blood to a patient, for example in dialysis applications, injecting air to the patient has to be avoided. Therefore, dialysis machines usually include sensors that identify air in their venous blood tube system and stop an ongoing therapy, if air is detected. A space-resolved method is advantageous in this context to the effect that the air volume in the air bubbles can be quantified more exactly and thus a risk for patients can be better assessed. Air bubbles in the blood are inhomogeneities which absorb light less strongly than the blood itself and which at the same time have a low refractive index. With the aid of said two characteristics and when an appropriate wavelength for the incident light is selected, preferably in the infrared spectral range, detection of air bubbles in blood is possible and air bubbles are detectable by an optical detection system as described before.

Furthermore, blood clots differ from liquid blood by their absorption, their refractive index and the light scattering resulting therefrom. For this reason, blood clots may be identified and quantified with the aid of space-resolved optical measurements. What is critical to the patient is a blood clot forming in the tube system or dialyzer which detaches and gets into the patient via the venous line. An optical detection system as afore-described is capable of identifying a blood clot migrating or flowing through the venous line and of preventing the supply thereof to the patient.

The optical detection system as afore-described moreover is applicable for the detection of impurities in NaCl solution. Occasionally, even when most care is taken, impurities from the production process happen to remain in a tube system or dialyzer. Said impurities are dissolved when flushing the tube system and the dialyzer and are gradually flushed out. Such impurities, which frequently are present in the form of plastic fibers or plastic flakes, can be detected due to their higher refractive index as compared to the ambient water by optical measurement resolved in space and time. When such impurities are detected during the flushing operation, an increase in the flushing volume may achieve complete flushing of said impurities and thus prevent foreign matter from being supplied to the patient during therapy.

It is equally possible that, due to the circumstances during a therapy, impurities are produced inside the tube system, e.g. by abrasion on the inside of the pump segment. Said impurities, too, can be detected due to their optical characteristics which are deviating from blood so that they can be prevented from being supplied to the patient.

As described afore and verified by experiment, improved evidence of air inclusions or impurities in the medium guided inside the tube (liquid in this case) can be provided and improved identification and measurement of the geometry of air inclusions or impurities in the medium can be obtained by a more homogenous illumination of the field of view inside the tube for an imaging/space-resolved sensor system in an optical detection system forming a detecting device for a medium inside a tube portion as afore-described.

This can be achieved, in accordance with the invention, by a detecting device for a medium inside a tube portion comprising at least one light source being arranged at a first position relative to a tube portion adapted to be transilluminated with light and being configured to irradiate light onto the tube portion, a detector unit being arranged at a second position relative to the tube portion and being configured to receive light from the at least one light source passed through the tube portion and to analyze a medium in the tube portion in a spatially resolving manner, and comprising a homogenizing device being arranged at a position between the at least one light source and the tube portion and being configured, for detecting and quantifying differences in brightness due to local differences of the medium inside the tube portion, to create a homogenous and/or isotropic distribution of the light from the at least one light source, before the light enters into the tube portion.

In the foregoing, the invention has been described by way of preferred embodiments. It is understood that details of the described preferred embodiments do not limit the invention as such and that various changes, modifications and/or equivalents obvious to those skilled in the art may be resulting all of which as such are within the scope of protection of the invention defined by the enclosed claims.

The invention claimed is:

1. A detecting device for a medium inside a tube portion, the detecting device comprising:
   at least one light source arranged at a first position relative to the tube portion adapted to be transilluminated with light and configured to irradiate light onto the tube portion in a light path;
   a detector unit arranged at a second position relative to the tube portion and configured to receive light from the at least one light source passed through the tube portion and to analyze a medium inside the tube portion in a spatially resolving manner;
   a homogenizing device arranged between the at least one light source and the tube portion and configured, for detecting and quantifying differences in brightness due to local differences of the medium inside the tube portion, to create at least one of a homogenous or isotropic distribution of the light from the at least one light source before the light enters the tube portion, the homogenizing device including a light absorbing substance introduced to the homogenizing device at predetermined concentrations to provide a variably light-absorbing function of the homogenizing device, the light absorbing substance introduced to the homogenizing device along a direction perpendicular to a transilluminating direction in predetermined areas of the homogenizing device; and
   first and second walls between which at least one of the at least one light source or the homogenizing device is arranged, wherein the first and second walls extend in a longitudinal direction bordering the light path and without interrupting the light path.

2. The detecting device according to claim 1, wherein the at least one light source is arranged on a first side of the tube portion and the detector unit is arranged on a second side of the tube portion so that the tube portion is located between the at least one light source and the detector unit to form a geometric arrangement for transmission measurement.

3. The detecting device according to claim 1, wherein the at least one light source and the detector unit are arranged on the same side of the tube portion at a predetermined angle relative to each other to form a geometric arrangement for reflection measurement.

4. The detecting device according to claim 1, wherein the homogenizing device is a scattering disk, a diffusor film or a transparent medium having a roughened surface.

5. The detecting device according to claim 1, wherein the homogenizing device is located as closely as possible to the tube portion.

6. The detecting device according to claim 1, further comprising: an imaging optical system positioned to be at least one of upstream of the detector unit or between the at least one light source and the homogenizing device.

7. The detecting device according to claim 1, wherein the detector unit has a field of view, and wherein spatial dimensions of the homogenizing device conform to spatial dimensions of the field of view of the detector unit.

8. The detecting device according to claim 1, wherein the at least one light source is configured to completely illuminate an expansion of the homogenizing device in a longitudinal direction of the tube portion.

9. The detecting device according to claim 8, wherein a shape of the at least one light source is adapted for complete illumination of the expansion of the homogenizing device in the longitudinal direction of the tube portion.

10. The detecting device according to claim 8, further comprising:
    at least one of a plurality of light source elements or a plurality of beam-forming elements positioned in a light path for complete illumination of the expansion of the homogenizing device in the longitudinal direction of the tube portion.

11. A medical apparatus comprising a detecting device according to claim 1, wherein the medical apparatus is a machine for extracorporeal blood treatment.

12. A detecting device for a medium inside a tube portion, the detecting device comprising:
    at least one light source arranged at a first position relative to the tube portion adapted to be transilluminated with light and configured to irradiate light onto the tube portion in a light path;
    a detector unit arranged at a second position relative to the tube portion and configured to receive light from the at least one light source passed through the tube portion and to analyze a medium inside the tube portion in a spatially resolving manner;
    a homogenizing device arranged between the at least one light source and the tube portion and configured, for detecting and quantifying differences in brightness due to local differences of the medium inside the tube portion, to create at least one of a homogenous or isotropic distribution of the light from the at least one light source before the light enters the tube portion, the homogenizing device including a light absorbing substance introduced to the homogenizing device at predetermined concentrations to provide a variably light-absorbing function of the homogenizing device, the light absorbing substance introduced to the homogenizing device along a direction perpendicular to a transilluminating direction in predetermined areas of the homogenizing device, wherein the homogenizing device is located as closely as possible to the tube portion; and first and second walls between which at least one of the at least one light source or the homogenizing device is arranged, wherein the first and second walls extend in a longitudinal direction bordering the light path and without interrupting the light path.

13. A detecting device for a medium inside a tube portion, the detecting device comprising:

at least one light source arranged at a first position relative to the tube portion adapted to be transilluminated with light and configured to irradiate light onto the tube portion;

a detector unit having a field of view, the detector unit arranged at a second position relative to the tube portion and configured to receive light from the at least one light source passed through the tube portion and to analyze a medium inside the tube portion in a spatially resolving manner;

a homogenizing device arranged between the at least one light source and the tube portion and configured, for detecting and quantifying differences in brightness due to local differences of the medium inside the tube portion, to create at least one of a homogenous or isotropic distribution of the light from the at least one light source before the light enters the tube portion, the homogenizing device including a light absorbing substance introduced to the homogenizing device at predetermined concentrations to provide a variably light-absorbing function of the homogenizing device, the light absorbing substance introduced to the homogenizing device along a direction perpendicular to a transilluminating direction in predetermined areas of the homogenizing device, and wherein spatial dimensions of the homogenizing device conform to spatial dimensions of the field of view of the detector unit.

* * * * *